(12) United States Patent
Denizoglu

(10) Patent No.: US 10,369,321 B2
(45) Date of Patent: Aug. 6, 2019

(54) VOICE THERAPY AND VOCAL TRAINING DEVICE

(71) Applicant: DOCTOR VOX SAGLIK HIZMETLERI VE MEDIKAL CIHAZLAR LIMITED SIRKETI, Ankara (TR)

(72) Inventor: Ilter Denizoglu, Izmir (TR)

(73) Assignee: DOCTOR VOX SAGLIK HIZMETLERI VE MEDIKAL CIHAZLAR LIMITED SIRKETI, Ankara (TR)

( * ) Notice: Subject to any disclaimer, the term of this patent is extended or adjusted under 35 U.S.C. 154(b) by 285 days.

(21) Appl. No.: 15/415,854

(22) Filed: Jan. 25, 2017

(65) Prior Publication Data
US 2018/0050169 A1    Feb. 22, 2018

(30) Foreign Application Priority Data
Aug. 19, 2016    (TR) .............................. 2016/11706 U

(51) Int. Cl.
| A61M 16/16 | (2006.01) |
|---|---|
| B65D 1/02 | (2006.01) |
| B65D 41/02 | (2006.01) |
| B65D 25/56 | (2006.01) |
| A45F 5/00 | (2006.01) |
| A61M 16/06 | (2006.01) |

(52) U.S. Cl.
CPC .............. *A61M 16/16* (2013.01); *A45F 5/00* (2013.01); *B65D 1/0223* (2013.01); *B65D 25/56* (2013.01); *B65D 41/02* (2013.01); *A61M 16/06* (2013.01)

(58) Field of Classification Search
CPC ................. A61M 16/16; A61M 16/06; A61M 2016/0661; A62B 7/02; A62B 7/14; A62B 9/003; A62B 18/02; A62B 18/025
See application file for complete search history.

(56) References Cited

U.S. PATENT DOCUMENTS

| 3,807,445 A * | 4/1974 | McPhee | A61M 16/0051 |
|---|---|---|---|
| | | | 137/557 |
| 3,825,000 A * | 7/1974 | Huggins | A61M 16/00 |
| | | | 128/200.11 |
| 4,367,182 A * | 1/1983 | Kienholz | A61M 16/16 |
| | | | 261/122.1 |
| 4,848,331 A * | 7/1989 | Northway-Meyer | ......... |
| | | | A61M 16/0488 |
| | | | 128/200.26 |

(Continued)

*Primary Examiner* — Jason E Flick
*Assistant Examiner* — Courtney B Fredrickson
(74) *Attorney, Agent, or Firm* — Gokalp Bayramoglu

(57) ABSTRACT

This invention relates to a voice therapy and vocal training device which allows performing both exhalation (phonation and breathing) and inhalation (humidifying and breathing) therapies and to humidify and treat vocal folds of a user. The aim of this invention is to provide a voice therapy and vocal training device which aids in carrying out many features together (all-in-one) such as performing voice trainings, humidification of vocal folds, and being used as an inhalation and a spray device. The voice therapy and vocal training device of the invention prevents water from going down the user's throat during inhalation thanks to its special design. Also disclosed is an oral mask which is able to be used with the voice therapy and vocal training device.

15 Claims, 14 Drawing Sheets

(56) References Cited

U.S. PATENT DOCUMENTS

| | | | | |
|---|---|---|---|---|
| 5,694,929 A | * | 12/1997 | Christopher | A61M 16/0488 128/205.25 |
| 7,077,154 B2 | * | 7/2006 | Jacobs | A61M 16/0666 128/201.23 |
| 2002/0092858 A1 | * | 7/2002 | Bowman | A45F 3/16 220/709 |
| 2005/0150495 A1 | * | 7/2005 | Rittner | A62B 18/025 128/205.13 |
| 2014/0251319 A1 | * | 9/2014 | Hoke-Kearns | A62B 9/003 128/200.14 |

* cited by examiner

VOICE THERAPY AND VOCAL TRAINING DEVICE

CROSS REFERENCE TO RELATED APPLICATION

This application is based on and claims priority to Turkish Utility Model application TR 2016/11706 filed on Aug. 19, 2016, the entire contents of which are incorporated herein by reference.

TECHNICAL FIELD

This invention relates to the portable voice therapy and vocal training device for treatment of voice disorders and training professional voice as well as humidification of vocal folds.

BACKGROUND ART

Vocology is the science and practice of human voice habilitation and rehabilitation. Vocology is a multidisciplinary science and has three main subspecialties: Basic Vocology, Clinical Vocology and Pedagogical Vocology. Basic Vocology is defined as science and practice of multidimensional and multilayered research, measure and assessment of human voice. Basic Vocology includes mostly laboratory study fields such as acoustics, aerodynamics, biomechanical modeling of human voice. In Clinical Vocology, diagnosis and treatment of voice disorders take place. Pedagogical Vocology is about developing and sustaining a healthy and effective voice keeping the singer in a proper performance state. Professional voice is the focus of pedagogic vocology. Professional voice users include not only teachers and call center workers who maintain their jobs using their voices but also actors, speakers and singers who use their voices for performance. Therefore, the invention has a wide range of relevant usage areas.

Sustainable professionalism is the basis for a professional voice user. For example, workforce loss of a teacher who has dysphonia results in serious occupational and social consequences if the situation is permanent or occurs frequently. Personally, dysphonia can be the end of professional life of a vocal artist. Dysphonia is also an important problem for non-vocal performer patients. Moreover, hydration and humidification are important factors for vocal fold vibration; poor lubrication of vocal fold mucosa lead to important phonatory problems.

The most frequently used voice therapy technique in this method is the Lax Vox voice therapy technique in the state of the art. Lax Vox voice therapy technique is a voice therapy technique that changes voice directly. It can be included in general methods as it can be used in different voice pathologies (Hyperfunctional/Hypofunctional voice disorders). Lax Vox is a holistic and cognitive approach which gives a multichannel biofeedback and is easily applicable. Lax Vox differs from other methods in terms of using different multi-directional and multi-layered voice therapy approaches (respiration-resonance-vibration pattern-posture and support) at the same time.

Flexible silicon tube used in Lax Vox technique has 30-35 cm length, 9-12 mm inner diameter and 12-13 mm outer diameter. Literature studies conducted with glass tubes on tube length make recommendations about patient's gender, being child-adult, and voice class. Length, which increases impedance matching between source and filter and provides the most comfortable working way of larynx, can be empirically tried for each patient (comfortably lowered larynx position, a feeling of vibration on the face) and the silicone tube can be shortened for each patient. During the application, a silicone tube is placed into a bottle having warm water 1 to 5 cm deep. Preferably, 500 cc plastic water bottles that can be obtained in the market as water containers can be used. Depth of water is adapted to the patient, 1-cm depth is sufficient at the first stage, but the depth can be changed in time. For example, the depth can be increased up to 15 cm in unilateral vocal cord paralysis.

Lax Vox Voice Therapy Technique basically includes 5 steps.

1. Preparation: (Good Posture, Muscle Relaxation, Direction, and Developing "Conscious Awareness")

During the preparation phase, posture, respiration and relaxation exercises are performed with patients to whom phoniatric diagnosis methods are applied and voice therapy decision is made. At this phase, the patient's conscious awareness of his/her voice and to "make the patient hear the voice coming out of his/her mouth" is tried to be developed.

Good posture affects voice more than presumed. Forward head posture which is particularly common in the society affects all phases of phonation negatively. Forward head posture alters the vocal tract shape and negatively affects vocal vibration pattern and ventilatory support during energy transformation of larynx. During Lax Vox, a posture in which the patient is in the sitting position, his/her head is in high position, his/her shoulders are in relaxed position and the sternum is in a high position and which is described as "noble posture" in singing pedagogy is preferred.

The patient sits relaxed but not slouched and tight but not stiffed. Especially relaxation of face and shoulders is ensured. Relaxation is a basic starting point for Lax Vox. The easiest way of changing contraction composition, which develops among some muscles ensuring any movement in the body, is relaxing these muscles and making their lengths close to relaxation lengths, then placing in the new contraction configuration. Relaxation of face (jaw and mimics), neck, shoulders, back, and chest muscles is helpful. Methods such as progressive relaxation, conscious medical hypnosis, etc. can be helpful for providing relaxation. It should not be forgotten that larynx has osteocartilaginous structure which does not have direct connection to skeletal system via articulation. Accordingly, it can be said that larynx is at a position in which it can be both free and pulled around among soft tissues of the neck thanks to connections and trachea support via muscles and tendons with skull base and prevertebral fascia. Relaxation is a key saving larynx from its ties. Relaxation can be controlled by palpation of particularly suprahyoid region after providing good posture. Palpation is taught to the patient and firstly breathing and then voice production can be ensured to the patient when suprahyoid region is relaxed. Downward movement of the larynx is shown to the patient in a mirror and the patient can be asked to stay like this.

When proper posture and relaxation are provided, the Lax Vox tube is released into the bottle. The patient holds Lax Vox tube between front incisor teeth (so as to pass incisor teeth a few mm) and closes the lips around the tube loosely without contraction as if saying /u/ so as not to allow air leakage. Firstly, the patient can be asked to do bubbling without phonation in order to raise awareness. Meanwhile, it is ensured that the bubbling of water can be felt in the cheeks. The way of this is to relax the cheeks. The image of "silly face" used in singing lessons can be useful. It is particularly asked not to lift eyebrows (there is an unexplainable weird connection between eyebrows and larynx; it is hard to lower larynx while eyebrows are raised!). Cheeks are required to be relaxed in order to feel vibrations in cheeks that occur by water bubbling just as occurrence of this vibration in the throat is possible by the relaxation of supraglottic structures. This situation can be used on the contrary; throat relaxation does not often yield a result for the patient because the patient is he/she not aware of stiffness in the throat. When the patient is asked to feel vibrations in the throat, it can be seen that the larynx has been lowered to comfortable vertical height.

Respiration is a subject that is not very practical to be applied directly to patients who are not professional voice users and particularly not vocal trainers during voice therapy. Although some cults express otherwise, respiration techniques have been developed in years and they are hard to change (use in real life outside the therapy room). Direct efforts and exercises related to breathing techniques mostly for people who are not professional voice users can result in weariness and with the ending of therapy. Lax Vox directs breathing indirectly instead of confusing the patient with too many instructions at the same time. Simulating breath to warm breath or breath exhaled while fogging up the glass is very effective (exhaling as if vocalizing /hhh/ can be useful but it should not be turned into whispering). Exhalation like such is directed to the abdominal and lumbar muscles. Besides, it can be recommended to patients, who have high-level awareness of voice and body, not heaving sternum during respiration. It should not be forgotten that a good singing breath is the one that is not seen, heard and felt by outsiders. After exhalation, inhalation is made nasally, expanding and comfortably. Expansion feeling is felt especially towards lower chest and waist as expressed in singing techniques.

Patients who can bubble water easily is asked to control the speed of bubbling. At this step, particularly vocal trainers can be recommended "seeing" and "counting" their breaths via just bubbling water. While doing that they are told to bubble calmly at certain numbers (approximately countable) and without spraying water out. Counting bubbles in the water approximately is the expression of how much air is consumed during phonation. Then, increasing and reducing of bubble speed in a controlled manner can be asked. Accordingly, many patients can raise awareness about their own breaths and abdominodiaphragmatic control can be sensitized.

Attention of the patient should be taken to the beginning and ending of exhalation. Glottal closure is required not to be seen in both cases. Closing and opening of breath in the glottis region during phonation activate laryngeal valve mechanisms and beginning phonation with hard glottal attack can result in hyperfunction. In order to understand hard glottal attacks better, the patient is asked to strain his/her voice and make a glottal pop sound voluntarily while his/her mouth is open. If the patient understands what glottal control is well, progress can be made in this matter.

2. Blowing Sound into Water

The Lax Vox silicone tube is dipped into the water. The depth of water is 1-2 cm at first for depressurizing. An end of the tube is placed so as to extend a few mm above tongue between incisor teeth. Considering the position of tongue inside the mouth, it should be relaxed so as to slightly touch behind lower incisor teeth. Tongue stiffness can be controlled by suprahyoid palpation. Tube is enclosed with lips (it is recommended to use humid parts of lips) without tightening. During the process, there should not be any leak around the tube and it is recommended to the patient to shape his/her lips as if saying a loose /ü/.

The patient is asked to create noise by blowing into water slowly and in mid tones. This tone can be practically 260 Hz for women which is known as middle Do (C4 note sound) while 130 Hz (C3 note sound) for men which is one octave below. Preferably, throat is opened and /o/ or /u/ sounds that lowers the larynx are made; at the same time therapists give examples with their voice and directs the patient by listening to his/her the patient's voice. Patients who start phonation with hard glottal attack are asked to add a "small" /h/ for softening the attack. Firstly, /h/ can be vocalized apparently as /HHHUUU/, and then it becomes inaudible and can be considered as if /hUUUU/.

Pitch of voice is also required to be considered. Particularly, patients with hyperfunctional voice disorder having vocal fold nodule start with high pitched voice out of habit of ranting. Stiff vocal system limits gliding pitches from high to low by glissando and the lowest voice which can be produced by the patient is around the middle of his/her own voice limits. Therefore, the patient may be required to be introduced with several techniques by which he/she can find natural fundamental frequency (primitive voice). Vibrations of bubbling can mask hyperfunctional voice mechanism all by itself and the patient can find his/her own primitive voice while bubbling. Other voice therapy techniques are made use of if necessary; for example, using vegetative functions (cough, yawn-sigh, laugh, etc.) can be helpful.

Some patients cannot make bubbles in the water by leaking air from the nose while bubbling; phonation is required to be ensured by closing palate. Sometimes only air can be blown without producing voice and the therapist can easily overcome this difficulty by giving examples.

During Lax Vox, auditory, visual and kinesthetic biofeedback mechanism work. The patient hears his/her voice better and feels better with vibrations. Besides, he/she sees his/her breath during the phonation in bubbles. The patient is suggested to bubble water with only breathing and then bubble with voice without confusing the count of breaths. Therefore, it is shown that too much air is not required to vocalize. It is possible to ensure full glottal closure, control undesired air leaks and increase efficiency at the first step.

3. Finding the Target Voice

At the step of patient recognition in the sound laboratory, generally the therapist has a voice (target voice) foreseen for the patient in his/her mind. At first, the patient is tried to produce a voice close to the target. The patient can produce monotone, even robotic voice. It should not be forgotten that it is impossible to proceed to the next step without achieving target voice. Lax Vox allows a patient to control functions of an organ which is not seen or cannot be touched by the patient by more powerful biofeedbacks. During the process, the patient has a "device" in his/her hand and his/her awareness and focusing increase using the device.

Even if the target voice has a single tone, the voice is expanded using the same phonation (at the same time, the voice produced by the patient is listened constantly and timbre change is prevented) when it is found. Accordingly, the patient is asked to bubble water with voices /hooo/ or /huuu/—keeping the bubbles going—so as to produce short voices. In order to raise awareness of the patient, questions (e.g. Which muscles are working? What do you feel?) are asked to the patient and the patient participates in the treatment actively not passively. Then, the voice is continued while maintaining the same tone and timbre. Bubbling with voice continues until gasp of breath and the patient is asked to stop phonation before gasping when he/she has difficulty in continuing the action. Questions for raising awareness (e.g. Which muscles are retracting?) can be asked. Staccato exercises can be started when the same tone is ensured to be maintained for a long time. The patient is asked to vocalize /oo oo ooo/ repeatedly for this (again at the same pitch and timbre). At the same time, the patient is ensured to listen to his/her voice carefully and to realize the difference that occurs due to the new muscle usage technique.

Attention should be given when the target voice begins to emerge. If the patient does not accept the voice, which can be foreign and far from his/her regular timbre, therapy process ends. Therefore, it is necessary to impose on the patient at this step that target voice is convenient, natural and can be easily accepted by the environment. Discussing patient on the fact that this voice is "real" and the other one is a mask, real "honesty" can only be ensured by this way, and winning the discussion are necessary to proceed to the next step. It is impossible to proceed in spite of the patient in voice therapy.

Finding target voice is not an easily achievable situation in each patient. Knowledge, experience and skills of therapist will be helpful. The therapist can vocalize voice tone he/she is foreseen by imitation and the patient can hear it. Methods of finding primitive voice (using mood states in which involuntary voices are produced such as being surprised, laughing, coughing, getting angry) can be tried in the environment without tube. A comfortable tone and timbre close to primitive voice is tried to be found. It can be asked to the patient, who is able to keep vocalizing primitive voice in the environment, to do phonation without interruption and not to change the timbre while continuing.

4. Improving the New Voice that has been Found

After obtaining the target voice, this new voice should no longer be a "foreign voice" and should be developed in order to be transferred to daily life. Target voice should be expanded in different pitches and loudness as well as in different resonances and articulations. The following exercises can be carried out to achieve this.

Some exercises are carried out in order to glide pitches up and down:

Glissando exercise: gliding voice without interruption from high pitch and to a comfortable low pitch. After that, reverse exercise from low pitch to high pitch can be done.

Staccato exercise: applying the same pitch change intermittently. However, glottis should be open while starting the voice and the voice should not be started with straining movement. During phonation, glottis should not be closed and should not return to strained position. Abdominodiaphragmatic control of airflow can be provided by balanced glottal attack. Reverse exercises can be done in order to raise conscious awareness of glottal closure by the patient. It can be asked from the patient to strain hard and to feel what is going on in his/her throat consciously. This can be repeated when the patient strains hard and releases his/her breath. At the same time, an additional feedback can be obtained by making the patient listen to the glottal click sound which is produced when the glottis opens due to high subglottal pressure.

Messa di voce is one of the basic exercises used in classical singing. The purpose is to ensure the balance between registers and create laryngeal stability. Loudness is tried to be increased and reduced while sustaining the same note. Similarly, the pitch can be made high and low without changing the loudness level. Lax Vox technique allows using this basic singing exercises in both ways.

Loudness of voice is increased and reduced in a comfortable pitch without changing the pitch.

The voice is glided from high pitch to low pitch without making any change in the loudness.

It is also possible to change resistance by phonation increasing and reducing the water amount in the bottle without changing pitch of voice.

Doing Mesa di Voce exercise in such a controlled and practical way has been particularly approved by singers.

The exercises are repeated by changing water depth gradually. The depth in which the patient feels comfortable most can be sustained. Apart from these specific purposes, it is recommended not to exceed a depth of 5-6 cm. This is because, subglottal pressure amount which is needed for comfortable phonation is around these levels.

Phonation is continued gradually by pulling the tube out of the water. Continuing phonation as if carrying out phonation outside the tube means that the same voice can be sustained without using physical advantages of Lax Vox Technique such as increasing inertance and extending the vocal tract. Different methods can be tried in order to ensure this. During phonation to the tube, lips enclosing the tube are slightly opened so as not to allow air leakage and during this time, not only water bubbling continues but voice is produced outside the device. This leakage is increased gradually but timbre of the voice should not absolutely be changed. If timbre of the voice changes while the phonation "leakage" is increased, the patient should return to the previous step and the leakage is reduced or full closure is ensured again, thus, correct timbre should be achieved. Leaking voice from the lips increasing gradually is achieved while the tube is in the mouth without bubbling. Finally, the tube is pulled out of the water and the same pitch and timbre are continued.

When open mouth phonation without tube is started, target voice should be produced at the limited pitch range comfortably. The patient starts to adapt himself to new voice and adopt new voice.

The patient is taught to be able to use similar mechanism without the tube via semioccluded vocal tract exercises. Lip trills, tongue trills, and feeling vibration in lips via humming are helpful exercises in this regard.

Pitch and loudness are changed and voice limits are expanded protecting the same voice. At this step, tube can be used again and phonation can be carried out in water and the external environment alternately.

5. Adopting the New Voice

Producing target voice only in the therapy room or during exercises does not make sense. When the patient starts to use the voice in daily life, it is possible to talk about the successful conclusion of the therapy. After finding target voice and expanding voice limits, motor learning principles that are used in many voice therapy techniques are applied:

Syllables-words-short sentences are formed by "new muscle technique" (Counting numbers, name, good morning, etc.)

Habit is formed by reading aloud (newspaper, book)

Conversational speech

Every voice therapy method is terminated as planned within a certain period. However, it should not be forgotten that voice therapy depends on the therapist (personal characteristics of the therapist, working environment, methods he/she applies, etc.), disease (etiology, disease severity, etc.) and the patients taking the therapy (voice usage level, therapy adherence, willingness of changing the voice, working determination, etc.); and dynamic and multi-directional approach should not be left considering that the rules can be changed by the therapist (and the patient). Voice therapy duration can be one or a few sessions in glottal closure disorder of professional singer due to minor technical glide while it can take months in unilateral vocal cord paralysis.

Lax Vox technique can be applied at different times according to the disease and the patient. In Lax Vox Voice Therapy Technique, home exercises are given for only one minute in an hour (10-12 times in a day) at the beginning and the patient is recommended to apply twice a week at first few sessions. It is clear that wrong exercises do not provide benefit; however, the patient may not be able to understand what he/she may have done wrong. Therefore, the first sessions can be performed with intervals of a few days. When it is certain that the patient does correct exercises with the desired voice, the time is increased to 3-5 minutes. After every session, home exercise program is developed. Accordingly, a program, by which the patient can take first measures on his/her own if he/she feels any problem after therapy, will be prepared. Especially for professional voice users, personalized and structured program is lifelong support for remembering using correct voice always, warming up and down the voice, and developing the voice.

The patient should get to the step of changing his/her voice and accepting a new one adopting the fact that voice "should come from brain not from larynx". When the patient can do exercises consciously and correctly, therapy sessions can be arranged more intermittently and appointments can be adjusted according to the course. Average therapy period of a patient that is applied regularly is approximately two months. Sessions are arranged twice a week for the first two weeks of these two months and once a week for the remaining time. A patient with unilateral vocal cord paralysis can be called for monthly controls until new muscle usage and adaptation of relevant muscles is created. A teacher getting therapy for vocal nodules can apply due to the same complaints a few years later. This time, the application is generally easier, therapy period which lasts for a few months can be performed in a few sessions.

Waiting for anatomical improvement cannot be necessarily expected for the termination of therapy or entering into e of checks at long intervals. Nodule sound disappears when glottal vibration pattern of a patient with fibrotic vocal nodules is recovered. Nodules can stay without making a big impact on vibration inside the mucosal wave. If the patient maintains a new vibration pattern, anatomical improvement is already expected within months.

Physiopathologic mechanisms used by Lax Vox Voice Therapy Technique are as follows in order of importance:
1. Increasing vocal tract inertance
2. Elongating length of vocal tract
3. Lowering larynx
4. Preventing secondary breathing muscles from overworking and facilitating abdominodiaphragmatic respiration
5. Increasing resonance of voice by staying away from tension of vocal tract and elongation of vocal tract via relaxation
6. Increasing kinesthetic sensitivity 1. Increasing Vocal Tract Inertance Inertance is a defining feature of the movement in a system. Inertance is a feature which facilitates the movement in the system and allows energy to stay in the system. For example, if a refrigerator standing on a ground needs to be moved. The refrigerator and the ground form a system. It is difficult to move the refrigerator because of strong friction with the ground. Wheels can be attached to the refrigerator for reducing the friction and preventing the removal of energy from the system by a resistor. Thus, the energy remains in the system and this feature (wheels attached to the refrigerator) can be defined as inertance. Therefore, inertance is a feature which stores energy in the system and facilitates the movement. Inertance can be defined in acoustics as a feature that facilitates the movement (depending on the pressure increase or decrease) of air column in a pipe. In such a system, inertance is directly proportional to the intensity of the air mass and length (of the pipe) while it is inversely proportional to the cross-sectional area of the pipe.

Human vocal tract can be likened to the system as a pipe that hosts moving air column. The source of acoustic energy in the system is transglottal airflow while the resistor in the system are formants which determine the harmonic composition of the voice. According to the linear source-filter theory that explains the formation of the human voice, acoustic energy leaving glottis enters vocal tract (disengages from glottis), the harmonic composition changes undergoing filtration with formants in the vocal tract, and finally leaves lips and moves to the external environment. Developments in vocology show that the situation was not so simple and revealed that the human vocal system is an extremely complicated nonlinear dynamic system at each stage.

According to the nonlinear source-filter theory, source and filter are in constant interaction and inertance increases intensity of this interaction. Acoustic energy leaving glottis undergoes filtration in the vocal tract while the filtration affects the glottal function at the same time. In other words, vocal tract (filter) changes the functioning of the source and resonates. The most important factor increasing the inertance in the vocal tract is high-pressure regions which are structured before acoustic energy. Inertive vocal tract means a vocal tract which has features increasing relationship between source and filter and facilitating vibration function accordingly. The acoustic results of an inertive vocal tract which is structured by forming high-pressure region before voice source are as follows:
 Vocal cords approach each other in a more controlled, balanced and easy way
 Phonation limit pressure drops
 VFs open and close quickly/easily
 Maximum flow declination rate (MFDR) increases
 Loudness increases (without muscle power)
 Closed phase extends
 Focusing is brought forward
 Vibration efficiency increases In the opening phase of vocal folds, pressure (which is equal to atmospheric pressure until that moment) just above the vocal folds in supraglottic region increases. Although this process is natural, it is possible to benefit from advantages of this process by increasing supraglottal pressure increase more.

Particularly, applications of classical singing pedagogy can be made use of in order to structure inertive vocal tract. Stage plays including mix of songs and theatres were held to great communities in times in which there was no technological possibility (microphone, speaker, amplifier, etc.) to increase the loudness of voice. For this purpose, interpretation of nature was done with the artist's intuition and narrow space (epilarengeal tube) was formed in supraglottic region in order to increase inertance of the vocal tract long before being written by mathematical language. This application is the source of timbre heard in songs sung by classical singing technique and the roots of which date back to the 16th century. While epilarengeal tube is formed, epiglottis is approached to the front wall of hypopharynx and a narrow space is formed in supraglottic region. The narrowing in cross-sectional area increases inertance of the system. The most delicate part herein is to avoid contraction and narrowing of all hypopharynx which is known as 'false squillo' in Italian, shows acoustically similar effect but means hyperfunction for the vocal system. In particular, unnecessary contraction of ventricular folds is one of the most significant findings of hyperfunctional voice disorders. In open throat technique which gives the basic timbre of the bel canto technique, while epilarengeal tube is formed, larynx will be in comfortably lowered position and hypopharynx will contribute to resonance keeping it wide around epilarengeal tube. "Pre-yawning position" that is frequently used pedagogically is one of applications used for this purpose.

Singers can use semi-occluded vocal tract exercises to warm-up their voices and to find the "position of the voice". These exercises are tongue and lip trills and closed mouth (with hmmm) exercises which are used in resonance voice therapy technique. Semi-occluded vocal tract exercises help a singer to be ready for the performance by warming up vocal folds properly before the performance and sharing similar mechanisms with epilarengeal tube formation.

High pressure generated in the supraglottic region allows for opening of the vocal folds back easier and faster which are at the beginning of the opening phase with mechanical effect. In the closing phase, similar mechanical impact makes closure easier and faster. In the closing phase, transglottal airflow is reduced and cannot continue supraglottal airflow anymore at some point. So, the pressure directly above the vocal folds decreases. The decrease facilitates closure of vocal folds by approaching each other with a vacuum effect. Therefore, not only horizontal but vertical closure surfaces of vocal folds will increase.

In the vibration pattern, the flow, which is an indication of especially closure rate increases as an acoustic reflection of abovementioned change and obtained by reverse filtration, is maximum flow declination rate (MFDR) in the glottagram curve. Steep slope, which means that transglottal airflow is interrupted quickly in the closure phase and increases intensity of acoustic energy i.e. loudness, is one of the most important parameters. In other words, maximum flow declination rate which becomes steep as a result of inertive interaction is one of main parameters that increase efficiency in the conversion process of potential energy of compressed air into the acoustic energy. In other words, vocalization is provided more by imposing less mechanical stress on the vocal cord tissue. This is one of the ways of vocalizing louder with the same supraglottal pressure and trained elite singers are found to have high MFDR values. Phonation threshold pressure will decrease and closed phase will be lengthened.

Harmonics in tonal voice are periodical frequencies by which acoustic energy is removed. Since vibration efficiency is increased in inertive source-filter interaction, acoustic energy amount distributed to harmonics will increase, and the voice will be rich, sonorous and loud. Since the closure will be more balanced and full, it is possible to produce a voice that has strong and rich harmonic structure (as requested particularly in classical singing). The effect is obtained by narrowing in vocal tract which is provided by tube section partially and water pressure at a silicone tube's end dipped into water and the silicone tube is used in Lax Vox Voice Therapy Technique. Considering law of closed containers, place of high-pressure region will make the same effect with supraglottic placement. The depth of water can be adjusted by both the therapist and the patient himself easily. Voice can be blown 8-10 cm $H_2O$ pressure for strengthening the voice while 2-3 cm $H_2O$ will be sufficient for relaxing. Meanwhile, the patient will have the opportunity of performing phonation by means of trying to keep bubbling under control continuously, "seeing" the air amount coming out during phonation, and making use of visual biofeedback.

2. Elongating Length of Vocal Tract

Exercises done by elongating vocal tract are applied in treatment of hypofunctional and hyperfunctional voice disorders and hypernasality and in order to develop projection (moving) of voice via increasing voice quality. Particularly, glass tubes having 25-28 cm length and 8-9 mm inside diameter were used in Finnish phoniatry ecole back to Sovijärvi while glass tubes having 12 cm length, 10 mm inside diameter and described as "resonance tubes" were used by Spiessin in German phoniatry ecole. It is known that phonation facilitates, more resonant voice is produced, and vibrations are felt on face and lips during phonation by this way. It was detected during modeling studies that elongation of vocal tracts by resonance tubes increased inertance of vocal tract, increased interaction between source and filter, and decreased oscillation threshold pressure.

The most important physical effect of artificial elongation of the vocal tract is lowered first formant (F1). It is possible to increase transfer function of the vocal tract by getting formant frequencies close to fundamental frequency variation and (in different pitches) to the frequency of close harmonic by means of harmonic format tuning. Therefore, the pitch that is heard will be strengthened when F1 frequency approaches the fundamental frequency and spent effort will decrease. Finally, following effects are obtained using the method of elongating vocal tract:

F1 approaches to the fundamental frequency
Phonation threshold pressure decreases
Airflow rate decreases
Low-effort phonation is performed 3. Lowering the Larynx Macroscopic mass movement of larynx is a movement that takes place up and down through the neck. While in relaxation, the posture of larynx (vertical larynx position) is in interaction with different factors. This interaction involves personal anatomical differences, habits, vital functions (breathing, swallowing), talking and factors during singing such as resonance, registration, breath, posture and articulation. The vertical larynx position is included among the factors that determine the fundamental frequency, loudness and timbre affecting vocal tract resonance and the biomechanical properties of the vocal folds.

The technique of lowering the larynx has been applied in classical singing pedagogy for almost a century. According to the technique, larynx is kept at a "comfortable" lowered level; thus, larynx muscles are kept in a tension and length that is close to relaxation length of muscles. In parallel with development of phoniatry and singing acoustics, the effects of the technique are better understood. Larynx is mostly at high level in hyperfunctional voice disorders that are the most common pathology.

Downward movement of larynx in the trachea direction will result in relaxation of mucosa membrane and soft tissues in the larynx inner wall by gathering together towards tracheal mucosa. If we think the opposite, when the larynx is heightened, contraction and thinning of the tissues is a natural result. This relaxation will increase the vibration mass, and its acoustic reflection will be a decrease in the fundamental frequency (Fo). Medial mucosal surfaces will come into more integrated contact with the relaxation of the vocal folds mucosa; thus, they can interrupt airflow more efficiently. Therefore, extension of closed phase (CQ) is seen in the EGG. At the same time, closure of mucosal wave accelerates with the relaxation (the MFDR increases) and thus increase in volume is provided without subglottal pressure (Psub) change. This encourages flow phonation.

Subglottal pressure decrease makes great contribution to phonation economy. Efficiency will increase during the conversion of potential energy of compressed air in the lungs into acoustic energy by glottal transformation. Therefore, unnecessary tension in the neck and shoulders are decreased. Relaxation of suprahyoid muscles is like a domino effect. Larynx-hyoid bone-tongue close relation loosens, the tongue moves forward. Finally, the use of abdomino diaphragmatic respiration technique facilitates due to conscious-active relaxation of secondary respiration muscles.

Downward displacement of the larynx and the relaxation of the vocal tract cause an increase in the resonance volume. The enlargement is provided by not only elongation of vocal tract but also soft palatal rise (pre-yawn position), hypoplaryngeal enlargement, flattened ventricular folds, and anteriorly placed tongue base.

It is expected to have strong upper harmonics in low-pitched voices by rich harmonic composition, voice timber, which is known as chiaroscuro in classical singing. Phonation by lowering larynx technique is the most important instrument for this. Inertance of the vocal tract increases, the MFDR increases, and energy increase occurs in the upper partial in lowering larynx technique, which was introduced at the beginning of the $19^{th}$ century and is also known as "open throat method". Voice is produced in a richer and darker voice timbre with the decrease in formant frequencies in the lowering larynx technique, which prepares ground for fusion of chest and head registers.

Control of relaxed muscles is better than tense muscles. A comfortably lowered larynx position ensures relaxation in intrinsic laryngeal muscles, particularly thyroarytenoid muscle, free functioning, and participation in phonation in a more active and controlled way. Relaxed thyroarytenoid muscle is an important advantage for muscle movements at nuance level during especially professional voice usage. High vertical larynx position causes stylohyoid muscle shortness and since the situation affects negatively cricothyroid muscle a key determinant of the pitch in singing voice, anterior movement of the thyroid cartilage is facilitated thanks to comfortably lowered larynx.

Although these mechanisms appear to be difficult to apply when they are taken individually, they are like interrelated parts of a whole actually. The main aim of all voice therapies is to find the best voice which is possible within the patient's anatomic and physiologic capabilities. The most indispensable feature of mentioned "target voice" is phonation economy. The comfortably lowered larynx position provided during Lax Vox application provides important advantages in phonation economy by both anatomical and acoustic changes.

4. Abdominodiaphragmatic Respiration

The main idea of abdominodiaphragmatic respiration is the fact that energy generation and energy conversion mechanisms do not affect each other. For this purpose, relaxation of secondary breathing muscles (upper chest, shoulder, neck, etc.) which help respiration in practice is provided. As previously mentioned, this situation is actually important in singing pedagogy; because energy generation and energy redirection steps of sustainable professional voice affect phonation efficiency and allow to do free artistic expression. The freedom and controlled relaxation are provided in Lax Vox technique and sustained during the phonation.

Abdominodiaphragmatic respiration "technique" is a part of training since requirements are at elite voice user level in practices with professional singers. Lax Vox can be helpful at this point. Abdominodiaphragmatic respiration can be called as a natural result of Lax Vox technique. In professional voice users, Breath can be directed without distracting patient by emphasizing terms such as breathing technique, diaphragm, etc., and without confusing patient with complex functioning of the situation. For this purpose, simple suggestions such as pushing the belly out, stable sternum, relaxed shoulders can be helpful. While the patient is bubbling the water, he/she looks at the bubbling and follows that sternum is stable and belly is pulled in and pushed out at the same time.

5. Relaxation

Relaxation does not mean being completely loose and slouching down. Muscles should be dynamic but hyperfunctional tension should be avoided. A comfortable posture with a moderate support is a key for a good phonation. In order to perform a movement in optimal conditions, muscles which will perform the movement are expected to be in ideal relaxation length. Inappropriate posture changes and injuries this length. For example, hunchback's relaxation lengths of a front body muscles are shortened. In this situation, shortening weakness develops, i.e. muscles have weak contraction feature in the ideal relaxation lengths. On the contrary, back body muscles elongate and contraction weakness develops in the muscles. In other words, they lose their flexibility and their contraction forces decrease. The fact of basic muscle physiology also applies in the larynx.

Extrinsic muscles provide proper larynx posture by staying in the most appropriate tension in order to allow laryngeal intrinsic muscles to relax and adjust pitch, loudness and quality of voice freely. Head and neck posture should be appropriate for allowing extrinsic muscles (each one of them) to be in the appropriate contraction state and ideal relaxation length. Considering leverage systems balancing posture for entire body, head, in the head and neck system which acts as if the first-class lever, will affect entire body since it has the highest value of momentum. And vice versa, if one of countless microleverage systems providing body posture is broken, it affects all of the micro system like a domino effect, and also affects head and neck leverage system. Posture should not be seen as a body is posture seen when looking in the mirror with a narrow point of view. Therefore, posture, which is one of fundamental elements of singing pedagogy, is a factor which may affect the voice without realizing; but required emphasis is not often made of posture.

During Lax Vox, relaxed body posture is tried to be provided without losing the vigilance of the body. Meditation, hypnosis, postural techniques (Alexander, Feldenkrais, Pilates, Yoga, etc.) may be used. Passwords reminding relaxed state (floating head, silly face, etc.) can be beneficial. The purpose of all these is to change the functioning of nonlinear mechanisms that affect the voice in countless ways at one point (the initial state). In order to ensure aliveness, commands such as stable and high sternum, noble posture, relaxed shoulders can be used similarly to breathing (posture and breath are connected mechanisms). Lax Vox "device" can mask hyperfunctional voice gathering the primary attention of the patient. Then, feeling bubbling in the mouth and throat actually encourages relaxation, if these tissues relax, by making use of physical response which they will give against vibration by trembling.

6. Increasing Kinesthetic Sensitivity

A person, who steps inwardly while walking, has strong biofeedback mechanisms for correcting the habit. A person, who can see their feet, who can touch and feel while walking, can change the habit using visual and kinesthetic—proprioceptive biofeedback mechanisms. However, only audio biofeedback is generally present for a patient for training his/her voice. The power of audio biofeedback now decreases hearing the incorrect voice repeatedly. Lax Vox technique facilitates recognizing/feeling/manipulating subglottal pressure, ensures using resonance spaces, and facilitates pharyngeal/laryngeal relaxation developing vibration sensation.

There is no portable, standardized product in "all in one concept". There is no standardization of products sold like silicone pipe in the market, and there is no official channel, there is not any certification such as a CE certificate. The presence of silicone material is uncertain medically and products sold in the form of plastic pipe are not suitable for health.

There are also tubes designed for humidifying the vocal folds. These products have only humidifying effect and do not have any function related to voice.

SUMMARY OF THE INVENTION

The aim of this invention is to provide a voice therapy and vocal training device which provides many features together such as treatment of voice disorders, carrying out vocal training exercises (vocal muscle development, warming up and cooling down the voice, etc), humidification of vocal folds, and being used as an inhalation device.

The other aim of this invention is; the device is designed to fit neck of a standard 500 cc plastic/PET (or similar bottles made of glass and other materials) drinking water bottle. Thus, user could easily carry the device without a bottle.

The other aim of this invention is to provide a voice therapy and vocal training device which has a special design that prevents air leakage during inhalation and exhalation applications. If water level is between 1-6 (indicated on the device) spillage of water during blowing or aspiration during inhaling is possible Thus; especially for inhalation, water level should be between the levels 9-6 of the phonation tube.

Another purpose of this invention is to provide a voice therapy and vocal training device in which humidifying liquid can be used much more than conventional embodiments and which is an important supportive in the treatment of respiratory tract and vocal folds wherein essences, herbal and medical products can be added into the liquid.

BRIEF DESCRIPTION OF THE DRAWINGS

"Voice therapy and vocal training device", which is provided in order to reach the aim of this invention, is shown in an attached figure.

Figure 1:
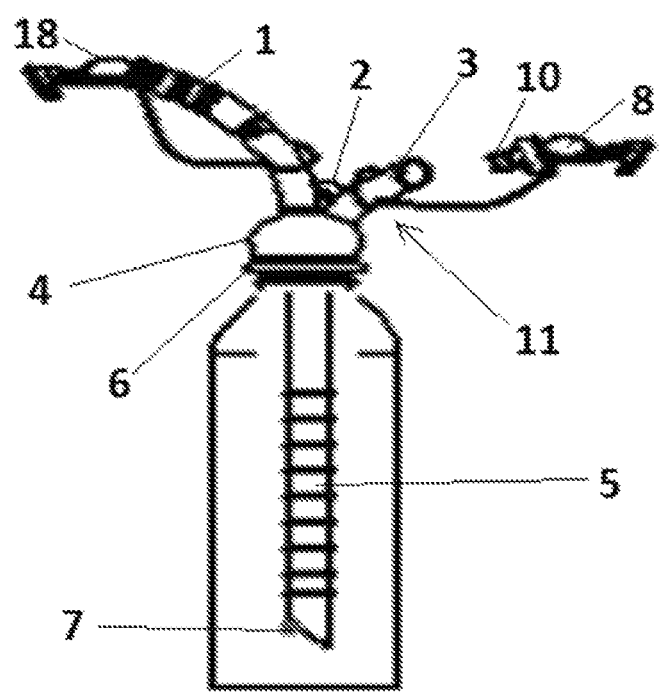
FIG. 1 is a schematic view of a voice therapy and vocal training device.
Figure 2:
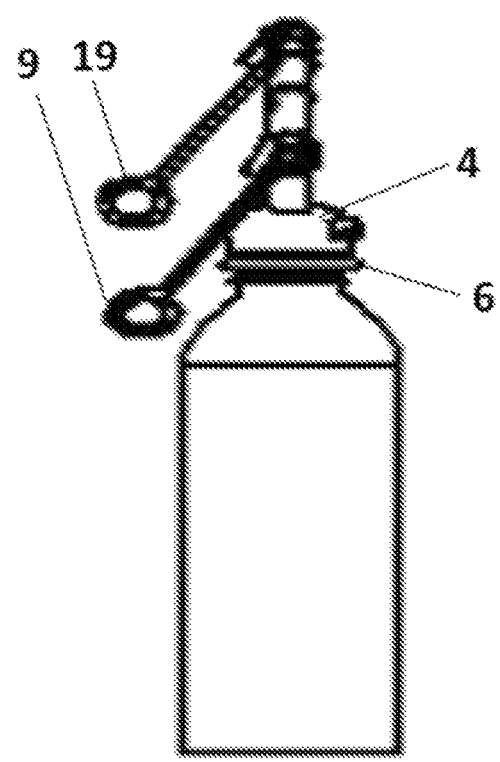
FIG. 2 is another schematic view of the voice therapy and vocal training device.
Figure 3:
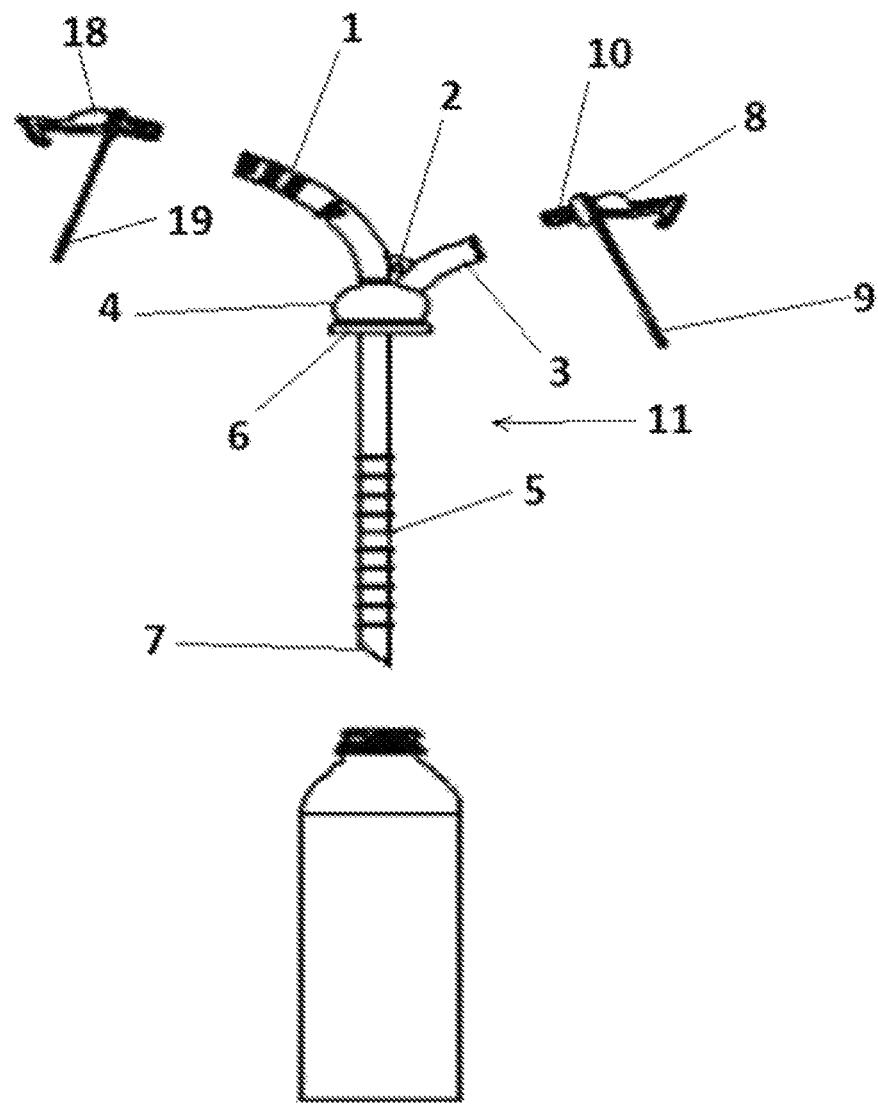
FIG. 3 is an exploded view of the voice therapy and vocal training device.
Figure 4:
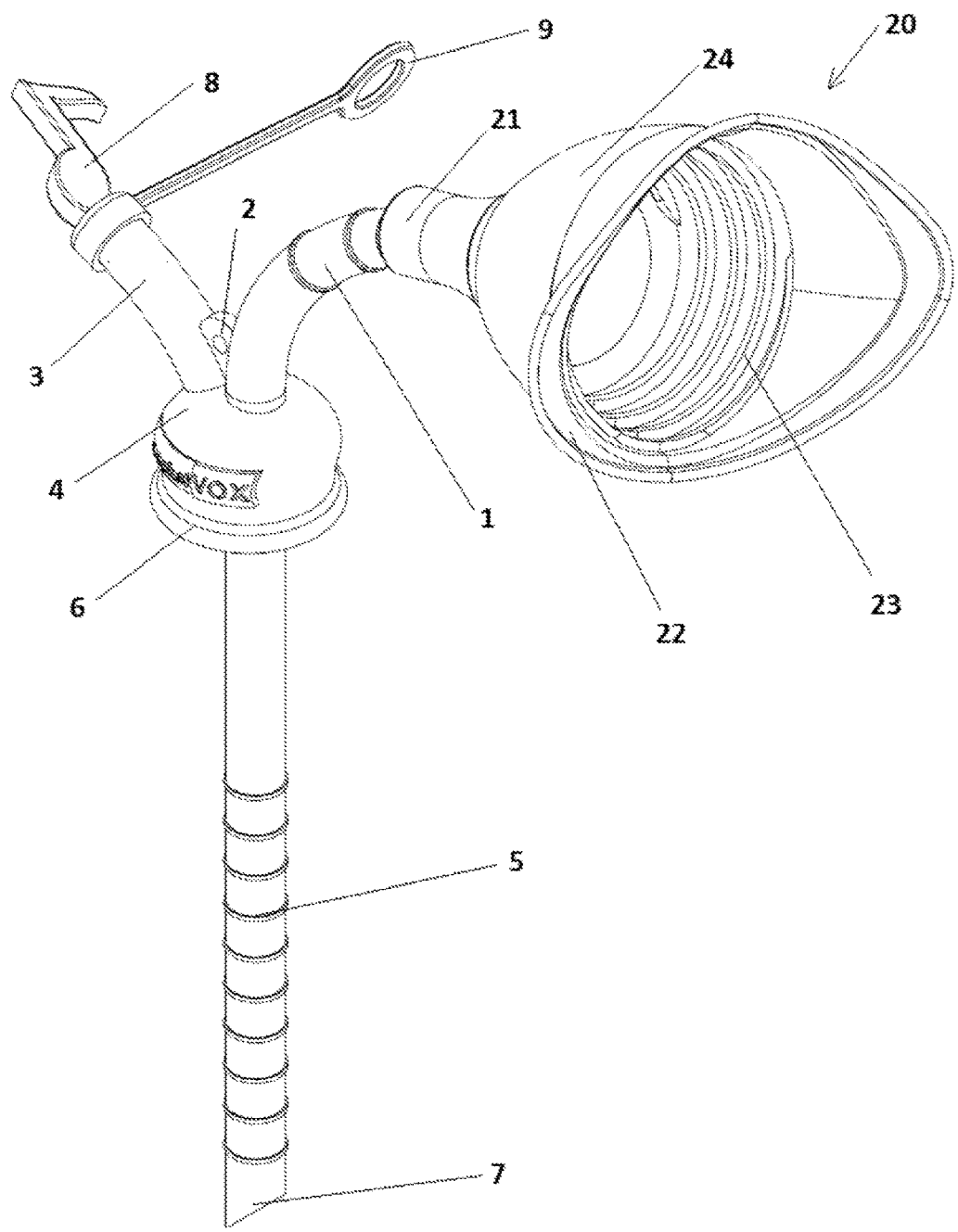
FIG. 4 is a perspective view of the voice therapy and vocal training device, which is used with a mask.
Figure 5:
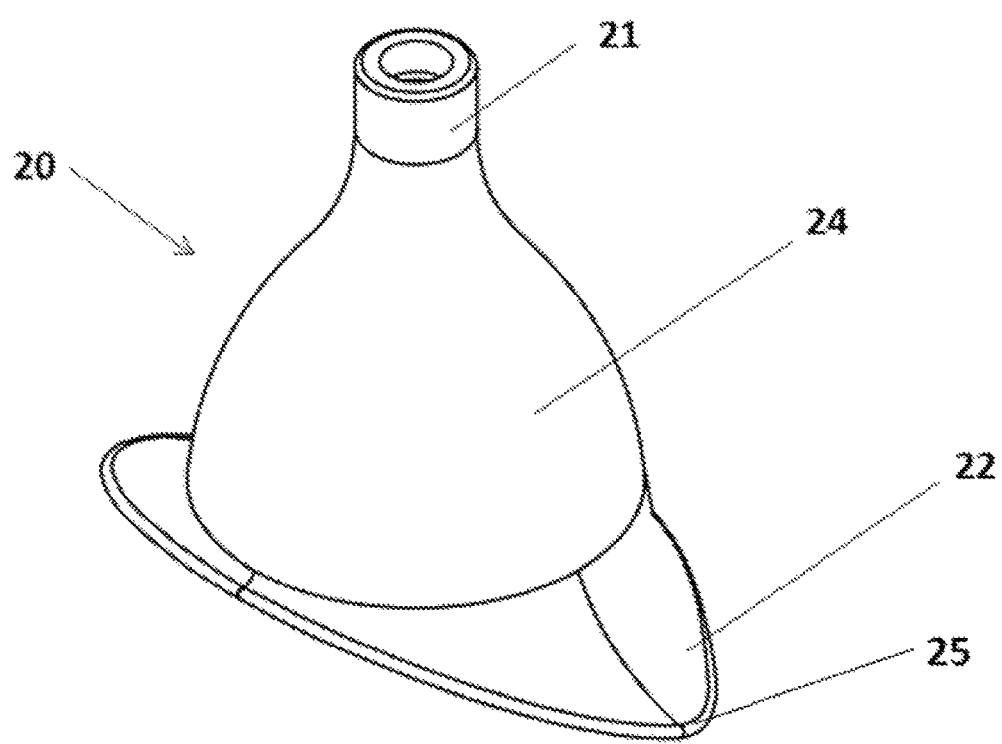
FIG. 5 is a perspective view of the mask.
Figure 6:
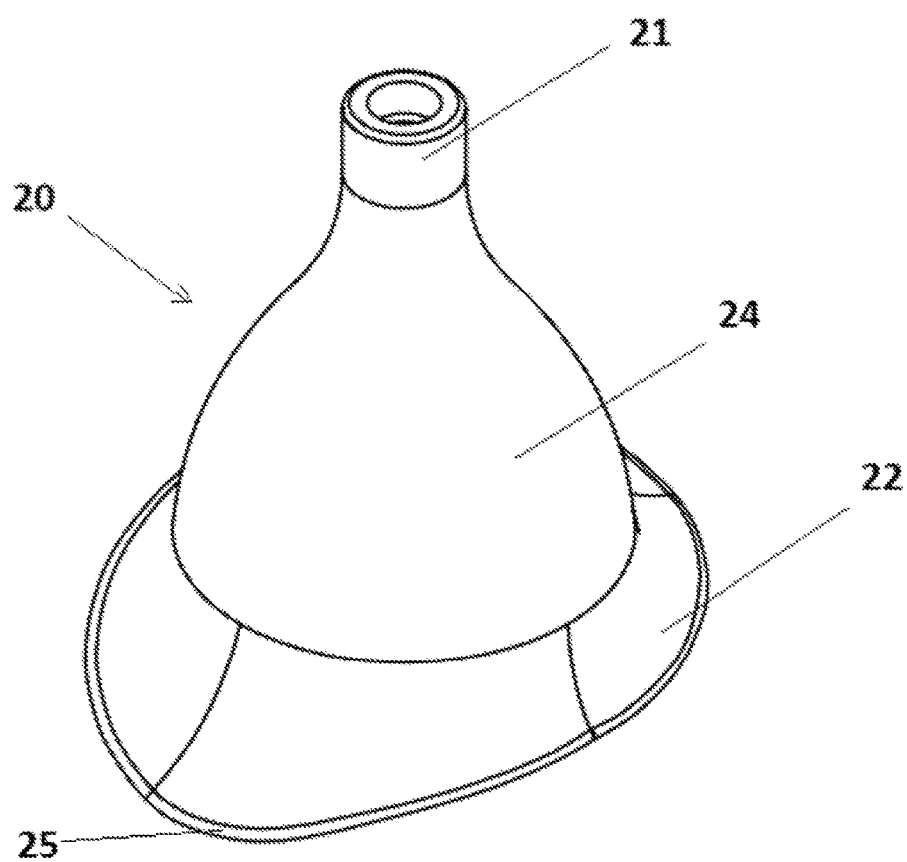
FIG. 6 is another perspective view of the mask.
Figure 7:
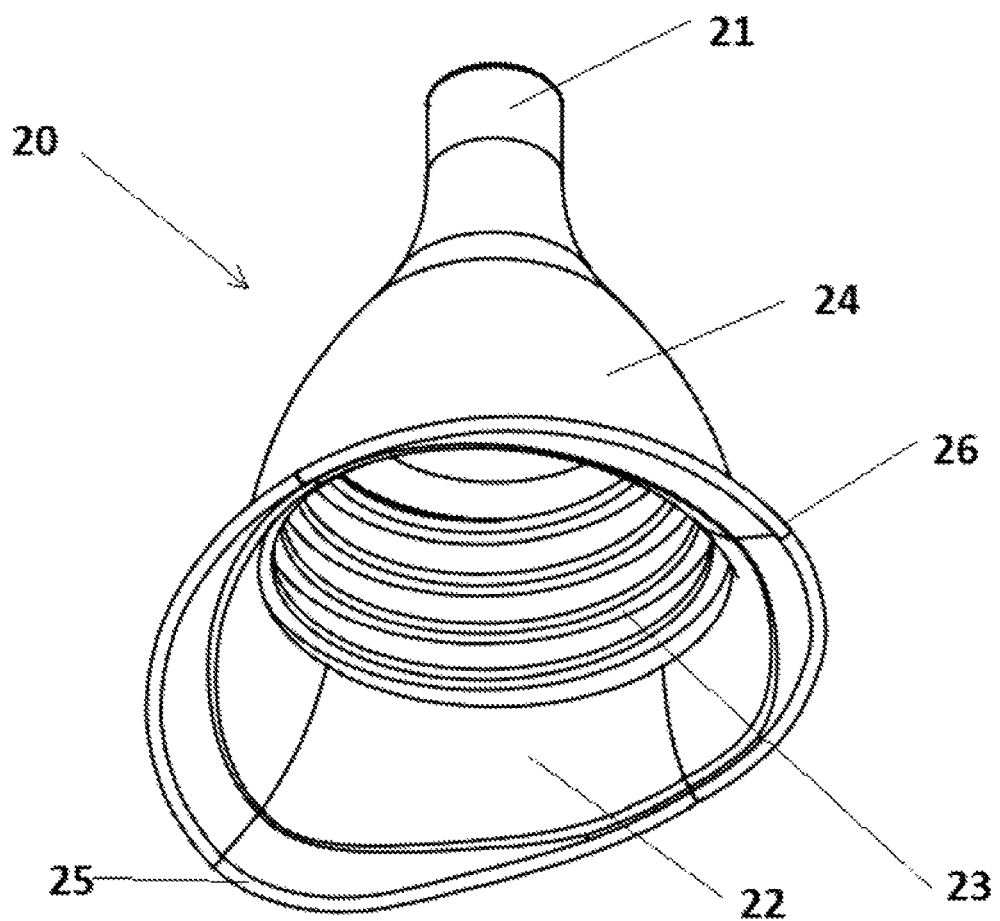
FIG. 7 is a bottom perspective view of the mask.
Figure 8:
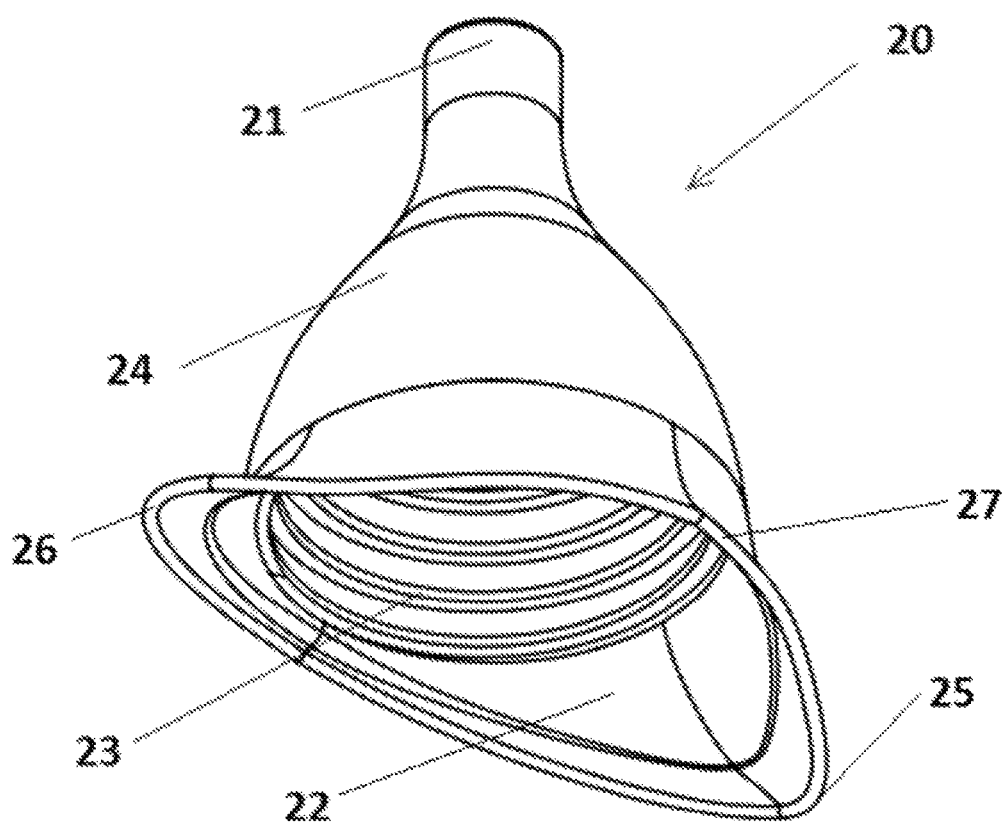
FIG. 8 is another bottom perspective view of the mask.
Figure 9:
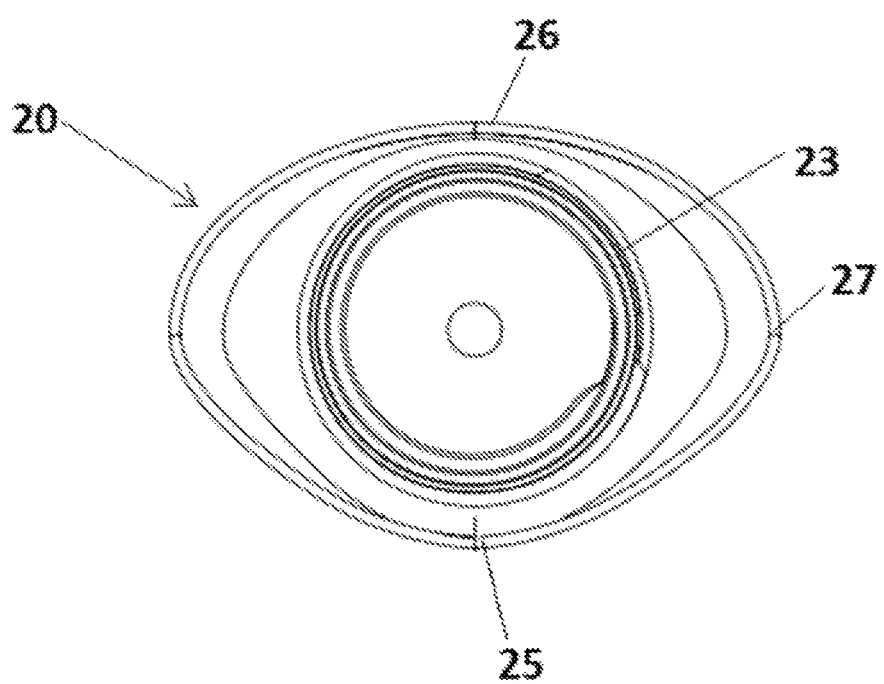
FIG. 9 is a bottom view of the mask.
Figure 10:
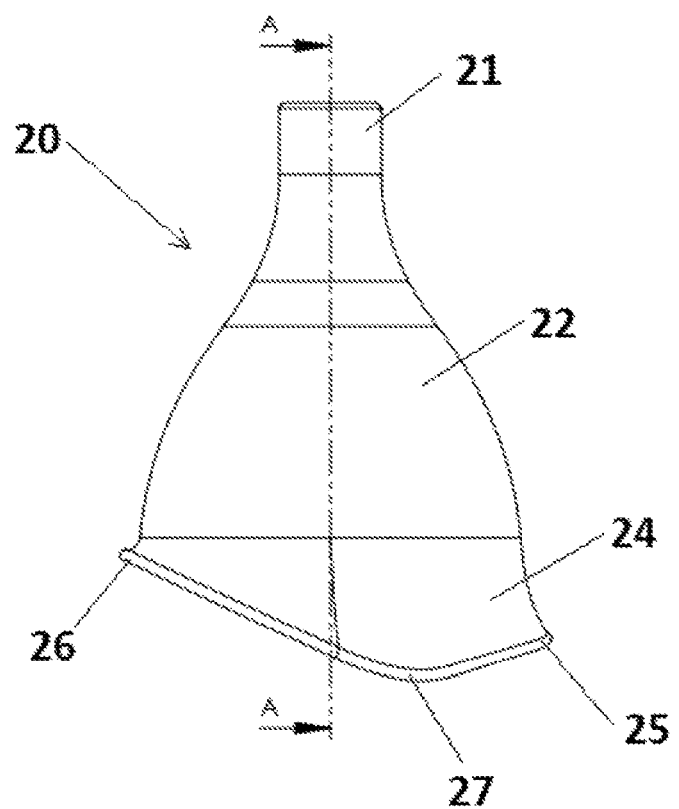
FIG. 10 is a side view of the mask.
Figure 11:
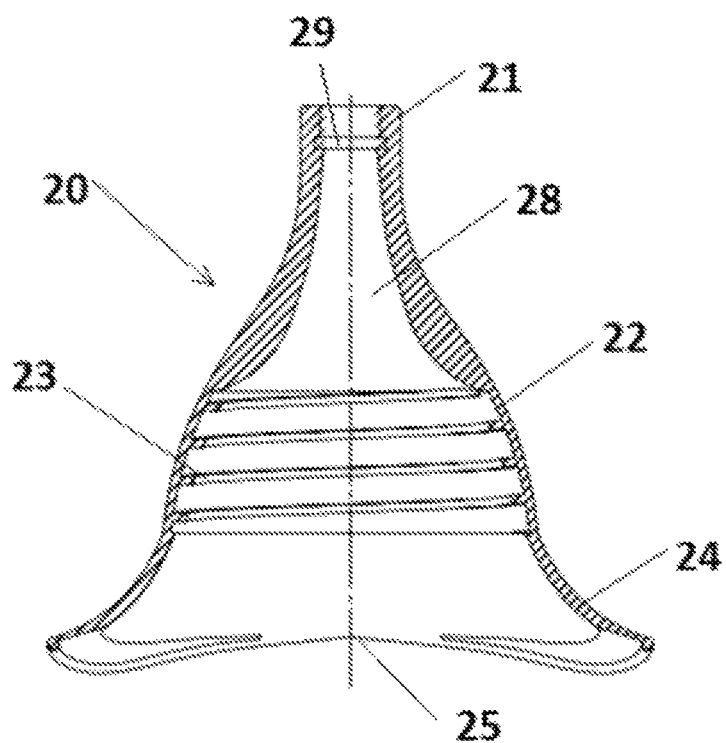
FIG. 11 is a cross sectional view of the mask, which is taken along line A-A in FIG. 10.

Parts in the figure have each been given reference numbers and the meanings of these numbers are as follows:
1. Phonation inlet
2. Neck strap hole
3. Inhalation outlet
4. Extension chamber
5. Water level marks
6. Multi-pass cap
7. Bubbling end
8. Note-shaped holder
9. Attachment ring
10. Plug
11. Voice therapy and vocal training device (pocketVox)
18. Note-shaped holder
19. Attachment ring
20. Oral mask (maskVOX)
21. Mask outlet
22. Mouthpiece
23. Spiral indentation
24. Mask body
25. Infranasal level
26. Infralabial level
27. Facial flap
28. Hyperbolic outlet channel
29. Locker groove
30. Oral mask

DETAILED DESCRIPTION OF THE EMBODIMENTS

The voice therapy and vocal training device of the invention which simultaneously humidifies the vocal folds and enables the training of vocal folds as treatment and/or therapy of professional vocal artists, and people who need to use their voice as part of their occupation or who have dysphonia basically comprises:
- at least one multi-pass cap suits a standard drinking water bottle which is made of PET, plastic or glass; that is for liquid to be used during therapy/treatment is poured in.
- at least one pipe unit which consists of at least a phonation inlet 1, which is inserted into liquid by passing through the neck of standard drinking water bottle which is made of PET, plastic or glass and extending inside the bottle which allows the user to carry out exercises for blowing and bubbling the water. The phonation pipe extends towards the neck of a standard water bottle that is sealingly joined and the end of the pipe does not come in contact with the base of the bottle; and at least an inhalation outlet 3 which is shorter pipe, ensures exercises for breathing and enables the transfer of the humid air to the upper airways of the patient.

In a preferred embodiment of the invention, a voice therapy and vocal training device 11 has a detachable feature to the neck of a standard drinking water bottle which is made of PET, plastic or glass, and this facilitates carrying and washing.

In a preferred embodiment of the invention, a voice therapy and vocal training device 11 is made of silicone, glass, plastic or silicone based durable materials that meet hygienic and acoustic features due to hygienic and durable features. In a preferred embodiment of the invention, a voice therapy and vocal training device 11 is made of styrene-butadiene block copolymer, random copolymer, polypropylene, polysulphone, polycarbonate, rigid PVC (polyvinyl chloride), rigid PET (polyethylene terephthalate), rigid silicone (medical grade) or glass materials, and at least one material that is selected from the group formed of the mixtures thereof.

In a preferred embodiment of the invention, a bubbling end 7, which has a protrusive structure, is provided at a phonation inlet's 1 end staying in the liquid in a water bottle for the purpose of ensuring bubbles after a user blows. In a preferred embodiment of the invention, the bubbling end 7 has an oblique cut.

In a preferred embodiment of the invention, a multi-pass cap 6, which is designed for fit various types or brands of standard drinking water bottles which are made of PET, plastic or glass.

In a preferred embodiment of the invention, water level marks 5 that are located on the outer surface of the phonation inlet 1 tube body direct a user in order to determine the liquid amount to be poured inside the bottle.

In a preferred embodiment of the invention, a neck strap hole 2 is provided on the extension chamber 4 of the voice therapy and vocal training device 11 which are in annular form, thereby allowing the users to pass through them an elastic material, such as a rope; wherein the users may wear said rope around their necks; as a result, the user can perform therapy without holding the (hands-free) voice therapy and vocal training device 11.

In a preferred embodiment of the invention, an inhalation outlet 3 ensures inhalation of herbal products, essences, and medical products that are added into the liquid inside a bottle together with humidified air, and allows a user to undergo treatment processes related to respiratory tracts effectively and easily.

A voice therapy and vocal training device of the invention is used for treatment of voice disorders, improvement of professional voice, and for the purpose of increasing voice efficiency, and has an "all in one" structure including portable, hygienic and standardized features. The invention is used in two ways:

1. Creating bubbles through a phonation inlet 1:
   Being able to do breathing exercises by watching stable air bubbles,
   Reaching the desired voice tone,
   Performing voice therapy,
   Improving functioning of vocal folds,
   Habilitation and rehabilitation of the professional voice
   Improving soft palatal functions,
   Improving lung capacity in some lung diseases.
2. Drawing air from an inhalation outlet 3:
   Humidifying vocal folds.
   Using some herbal products and medical products in airway treatments via dissolving them in water used in the system,
   Improving breathing technique for professional voice users.

Functioning mechanism of a voice therapy and vocal training device 11 of the invention operates in both ways as mentioned above. A phonation inlet 1 having 28 cm length and 8-10 mm diameter is the part for the functioning of vocal folds. Approximate length of a vocal tract in human body is about 14-17 cm. When adjusted properly, phonation into tube affects phonatory process positively by several acoustic-aerodynamic mechanisms. Generation of standing waves are more suitable when the tube length is in a proper proportion to the vocal tract length. For basses and alto sopranos (indicated by: al-ba), the length of the phonation tube is 28 cm (no cuts). For baritones and mezzosopranos (indicated by: me-ba) the user can cut the tube by scissors and adjust the length for himself/herself. For sopranos and tenors (indicated by so-te) it is 26 cm; for children (indicated by ch) it is 24 cm. Thus, more efficient and comfortable functioning of the vocal folds is possible. There are lines indicating cut-levels of a selected user on the phonation inlet 1.

An inhalation outlet 3 is used for the purpose of humidifying the vocal folds which are the secondary function of the voice therapy and vocal training device 11. While a user draws air through the inhalation outlet 3, bubbles will appear on the water surface under the effect of atmospheric pressure applied to the water surface through the open phonation inlet 1 and the intense air, which is humidified by passing through the water, moves towards the throat (the vocal folds) of the user. Thanks to atmospheric pressure which is applied on liquid/water through the phonation inlet 1, while a user draws air through the inhalation outlet 3, leakage of liquid/water inside the bottle to the mouth of the user is prevented by keeping water level between 9-6 on water level marks 5 of the voice therapy and vocal training device 11 and regular airflow is provided.

A voice therapy and vocal training device of the invention has many functions (voice therapy, breath therapy, vocal humidification and inhalation). One of the most important differences of the invention is that it provides a combination of both phonation and breathing exercises. Shape of the exit of the inhalation outlet 3, and correct adjustment of the water level in the water bottle prevent spillage even in severe blows. Also, the shape of the exit of the inhalation outlet 3, and correctly adjusted water level in the water bottle prevent aspiration of water inhalation. The tube of the phonation inlet 1 has approximately equal length to the vocal tract and has a rigid and smooth surface which does not absorb acoustic energy.

In addition to directing humid air to the vocal folds of a user according to the invention, humid air can be directed to the throat through the nose by means of a nasal mask to be used. Thus, humidification of inside the nose as well as vocal folds can be provided. Within the scope of therapies that are performed by humidifying the nose and the throat, herbal products, essences, and medical products to be able to be added to the liquid/water inside a container provide a user to undergo efficient and easy treatment process.

A voice therapy and vocal training device 11 has a feature of a compact device which can be carried by a voice professional, can pose his/her voice by warming via carrying out voice exercises, and can be used for the purpose of therapy in dysphonia, and can humidify the vocal folds by the same device. Structural features of the device 11 are designed (Water level should be kept between water level marks 5 9-6) so as to prevent liquid/water spillage from the device 11 during blowing and preventing aspiration of water during inhaling. Only humid air (and the substance added to the liquid/water), is inhaled during inhalation and aspiration of liquid/water is prevented from.

Thanks to the water level marks 5, which indicate back-pressure which affects phonation process during phonation into device. Thanks to the ergonomic design of a voice therapy and vocal training device 11 of the invention, the device 11 can be attachable to any standard drinking water bottle which is made of PET, plastic or glass, and can be washed in a dish washer. As it has been manufactured by a mold production method, it is cost effective following initial costs and its price is affordable by patients and professional voice users/performers. It is unique and convenient for international trade in addition to being convenient for distribution to national medical companies.

A voice therapy and vocal training device 11 is a device which can solve problems in the state of the art via acoustic and aerodynamic features as well as apply standard treatment. People, who undergo voice therapy or singing voice therapy, need a device which has hygienic features, which is portable and which can be cleaned easily. Since the device 11 of the invention can provide humidification of the vocal folds simultaneously, the device 11 bridges an important gap. Moreover, the product becomes more advantageous in daily use since it can be hygienically maintained and stored, it is practical. Comparing with conventional embodiments, the shape of the voice therapy and vocal training device 11 of the invention and its originality and professionalism in use are extremely suitable for convincing a patient about the effectivity of method and the device. These factors play an important role in the treatment process. Therefore, the design created by the invention will increase the patient's therapy adherence.

Tubes which are designed for humidification of the vocal folds have been provided in the state of the art. A certain amount of water, which is poured inside a bottle, provide humidification of breath and allow humidity to reach the vocal folds during inhalation. Comparing with these embodiments in the state of the art, high level of liquid/water amount and special design of a pipe unit in a voice therapy and vocal training device 11 of the invention provide intense humid air and more efficient treatment process. Also, thanks to the design of the voice therapy and vocal training device 11 of the invention comparing to conventional embodiments, it is not possible for water to be aspirated into airways of the user. A voice therapy and vocal training device 11 is a compact device which can use herbal or medical products that are added into liquid/water by means of respiration in addition to humidifying the vocal folds.

The most important feature of the voice therapy and vocal training device 11 of the invention is that features being provided by different systems can be provided by a single device (all in one). Within the use of the device 11 of the invention, it is possible to carry out voice training, and to humidify the vocal folds, and said device can also be used as an inhalation and spray device. While providing these functions, thanks to the design features, water splashing is prevented while air is blown in the device 11, and water is prevented from going down the throat of the user while drawing air (inhalation). Unlike existing technologies, the voice therapy and vocal training device 11 of the invention has the following features:

It is suitable for standard treatment protocols,
It can be used and maintained hygienically, it is standardized,
It provides practical carrying and protection features (It can be worn like a necklace and two hands can be free, it has a covered pocket and bag design),
Multi-pass cap 6 of the device 11 is easily fit to most of standard drinking water bottle which is made of PET, plastic or glass,
It provides intense humidification capacity,
The device 11 has a water level marks 5 showing water level in the bottle so as to prevent splashing,
The water level marks 5 can be used to adjust the backpressure,
It provides modular use (all in one).

The fact that higher amount of liquid/water is in a bottle of a voice therapy and vocal training device 11 compared to conventional embodiments, gives high humidification rate to the air during inhalation. This feature leads air to pass through the water and provides accumulation of intense humidity in the bottle space due to the spout.

The voice therapy and vocal training device 11 of the invention is made of silicone, plastic or silicone based durable materials that meet hygienic and acoustic features. Styrene-butadiene block copolymer, random copolymer, polypropylene, polysulphone, polycarbonate, rigid PVC, rigid PET, rigid silicone materials can be used as an alternative to this embodiment.

The voice therapy and vocal training device 11 of the invention can enable therapy to be carried out without using the user's hands (hands-free) thanks to neck strap hole 2. Also, a nasal mask, which is used, provides drawing air from the nose and humidifying the nose together with the vocal folds. Herbal products which will be added into the water inside the bottle can be used by inhalation.

The voice therapy and vocal training device 11 has a potential to address a large group of people. The absence of a similar product, domestically and abroad, provides the opening of a new field in terms of the market:

a) All voice professionals are in the target population. Teachers, singers, call center agents, lawyers, religious officials constitute a significant share among the users of the device of the invention. The workforce loss caused by the dysphonia in the target group can be reduced with a cheap and practical method thanks to therapies to be applied regularly by the voice therapy and vocal training device.

b) Use of the voice therapy and vocal training device 11 is an ideal and safe treatment device for patients with dysphonia apart from professional voice users. Medical companies can deliver this product to patients being treated for dysphonia. Hospitals providing voice therapy can provide the device to patients for therapeutic purposes keeping the product in their stocks.

c) Finally, the voice therapy and vocal training device 11 of the invention is an ideal product for the ones who want to use their voice correctly and effectively, and improve their communication skills.

A specially designed oral mask (maskVOX) can be used as an additional part of the pocketVOX device. MaskVOX is designed for LaxVox Voice therapy. In classical method, the therapy devices are taken into mouth so that the user cannot make articulatory movements properly. Normal masks (used in anesthesia) cover both face and nose and do not provide suitable use continuously during speaking or singing. MaskVOX provides continuously phonation by leaving the nose free for breathing.

As shown in FIGS. 4-13, oral mask 20 has mask outlet 21, mask body 22, and mouthpiece 24, which may be formed integrally or separately.

Mask outlet 21 can be connected to phonation inlet 1, for example, by using locker groove 29 (shown in FIG. 11), which is disposed in an inner wall of mask outlet 21 in order to lock the tip of the pocketVOX device when mounted. Those skilled in the art should understand, other appropriate method or means (such as snap-fit, interference fit, threaded connection) can be used to connect mask outlet 21 to phonation inlet 1.

Figure 12:
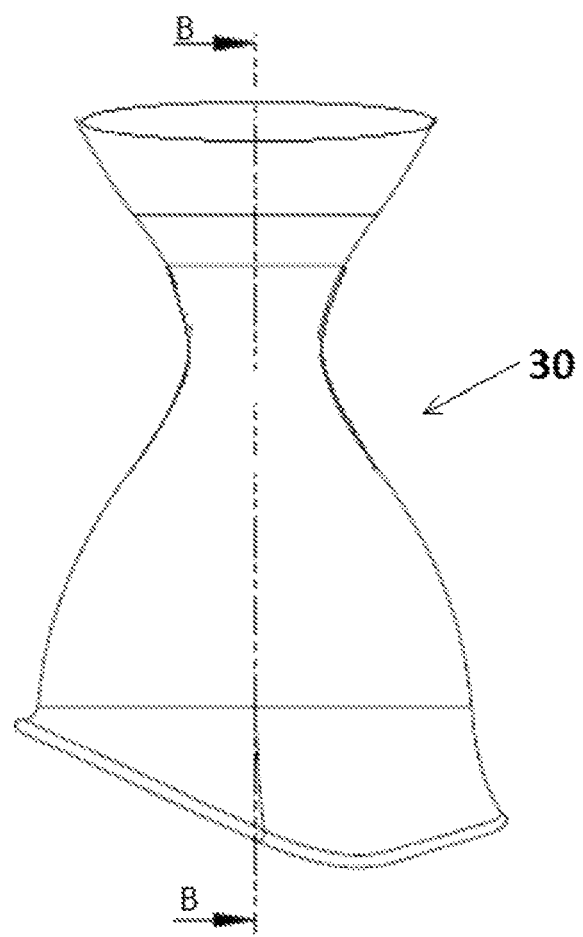
FIG. 12 is a side view of another embodiment of the mask.
Figure 13:
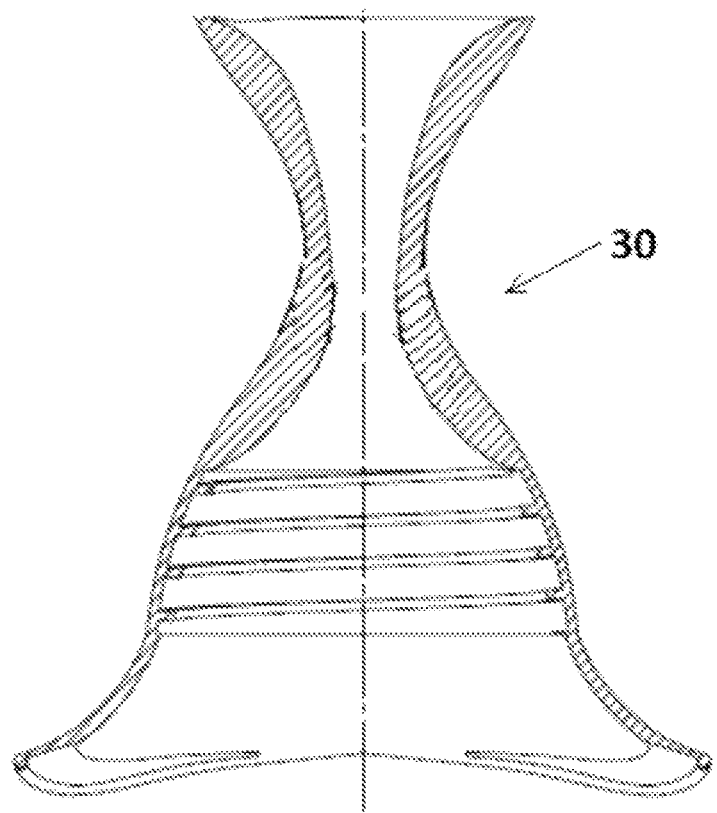
FIG. 13 is a cross sectional view of the mask, which is taken along line B-B in FIG. 12.
Figure 14:
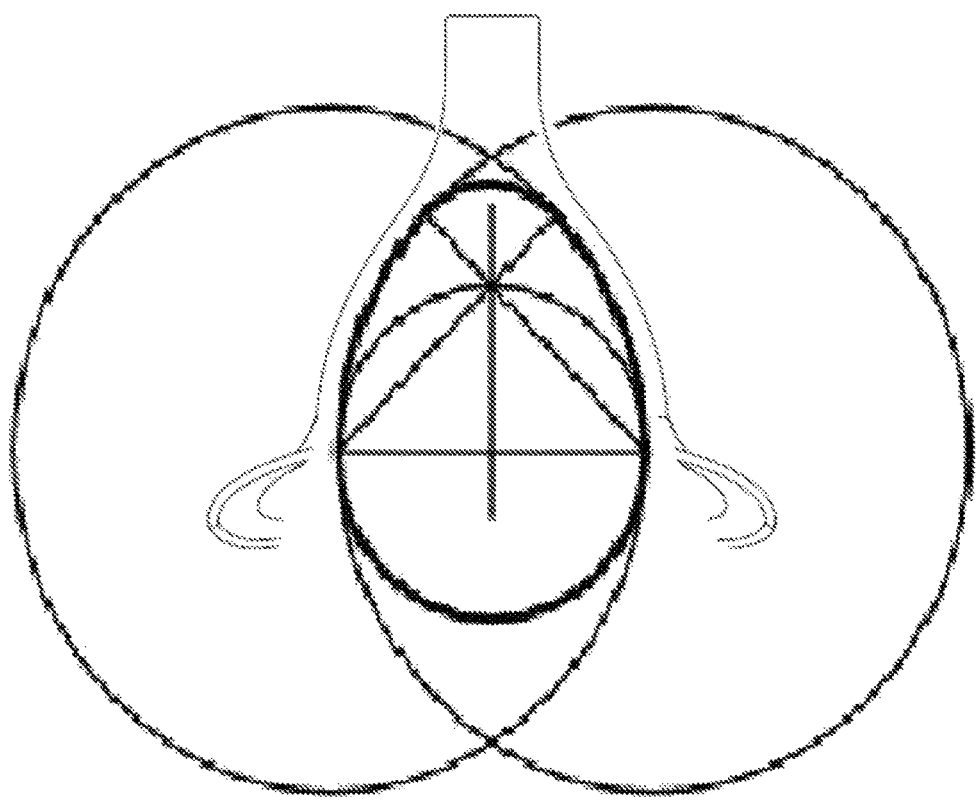
FIG. 14 shows the voice resonation during the use of the mask.

In some embodiment, mask outlet 21 has a hyperbolic shape. Mask outlet 21 of an outside-inward hyperbolic shape starts from the inner cavity. In order to increase the effect of backpressure, implosive effects of the hyperbole may be added to the shape of the outlet. The end of the inside-outward outlet pipe is designed to fit with the pocketVOX phonatory inlet. Those skilled in the art should understand, other suitable shape is also possible. For example, as shown in FIGS. 12-13, oral mask 30 has a hyperbole that is inversely mounted in an inside-outward fashion, then the acoustic properties change to be used as a voice resonator individually.

Mask body 22 has an egg shape to form a resonance cavity therein. The egg shape (measures coherent to Fibonacci series and golden ratio) resonance cavity consists spiral indentation 23 on the inner walls of the device. This spiral prominence can provide vortex in the cavity so as to strengthen the mask structure and provide acoustic effects. Those skilled in the art should understand, hyperbolic, oval, and other suitable shapes that can facilitate voice resonance or acoustic effects are also possible.

At the opposite end of mask outlet 21 is mouthpiece 24 for perioral fixation. This fit-for-all mouthpiece 24 is designed to fit for different types of face and mouth anatomy. As can be seen in the side view of oral mask 20 in FIG. 10, mouthpiece 24 includes infralabial level 26, infranasal level 25, and facial flap 27. This design can leave the nose free for breathing in use.

The invention claimed is:

1. A voice therapy and vocal training device which simultaneously humidifies vocal folds and enables training of the vocal folds, comprising:
   a water bottle;
   a multi-pass cap fitting a mouth of the water bottle;
   at least one phonation inlet connected to the multi-pass cap to allow blowing practices,
   wherein a length of the phonation inlet is in a predetermined proportion to that of a vocal tract of a user,
   a plurality of lines indicating cut-levels for different users on the phonation inlet,
   wherein when the multi-pass cap is fitted onto the mouth, the phonation inlet passes through the mouth and extends into liquid contained in the water bottle without contacting with a bottom of the water bottle; and
   at least one inhalation outlet connected to the multi-pass cap to allow exhalation practices and direct humid air being drawn from the water bottle to the vocal folds.

2. The voice therapy and vocal training device according to claim 1, wherein the phonation inlet and the inhalation outlet are made of silicone, glass, plastic or silicone based durable materials.

3. The voice therapy and vocal training device according to claim 1, wherein the phonation inlet and the inhalation outlet are made of styrene-butadiene block copolymer, random copolymer, polypropylene, polysulphone, polycarbonate, rigid PVC, rigid PET, rigid silicone materials, or at least one material that is chosen from a group that is formed from the mixtures thereof.

4. The voice therapy and vocal training device according to claim 1, wherein the phonation inlet and the inhalation outlet which are detachable to the water bottle are made of PET, plastic or glass.

5. The voice therapy and vocal training device according to claim 1, wherein a neck of the water bottle is made of PET, plastic or glass.

6. The voice therapy and vocal training device according to claim 1, further comprising at least one bubbling end, which is provided at the phonation inlet's end that is inserted in the liquid and which has a protrusive structure for creating bubbles after the user blows air.

7. The voice therapy and vocal training device according to claim 6, wherein the bubbling end has an oblique cut.

8. The voice therapy and vocal training device according to claim 1, further comprising at least one bubbling hole provided at the phonation inlet's end.

9. The voice therapy and vocal training device according to claim 1, wherein measuring lines are located on an outer surface of the phonation inlet as water level marks which allow the user to determine an amount of the liquid to be poured into the water bottle.

10. The voice therapy and vocal training device according to claim 1, further comprising a neck strap hole having a circular shape that can be attached to a rope.

11. The voice therapy and vocal training device according to claim 1, wherein the inhalation outlet enables inhalation of herbal products, essences, and medical products that are added into the liquid together with humidified air.

12. The voice therapy and vocal training device according to claim 1, wherein a tube which increases back pressure is provided inside the phonation inlet by means of being engaged to the phonation inlet's end which is inserted into the liquid.

13. The voice therapy and vocal training device according to claim 1, further comprising note-shaped holders to seal off the phonation inlet and the inhalation outlet.

14. The voice therapy and vocal training device according to claim 1, further comprising an oral mask connecting with the phonation inlet, wherein the oral mask further includes an egg-shaped body having a resonance cavity, a hyperbolic outlet located at one end of the egg-shaped body for connection with the phonation inlet, and a mouthpiece located at the other end of the egg-shaped body for perioral fixation.

15. The voice therapy and vocal training device according to claim 14, wherein the resonance cavity is provided with spiral indentations on an inner wall of the egg-shaped body.

* * * * *